(12) United States Patent
Atsumi et al.

(10) Patent No.: US 6,726,819 B2
(45) Date of Patent: *Apr. 27, 2004

(54) GAS SENSOR

(75) Inventors: Takayoshi Atsumi, Aichi (JP); Satoshi Ishikawa, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/769,393

(22) Filed: Jan. 26, 2001

(65) Prior Publication Data

US 2002/0100687 A1 Aug. 1, 2002

(51) Int. Cl.[7] .............................................. G01N 27/407
(52) U.S. Cl. ...................................... 204/428; 204/424
(58) Field of Search ................................. 204/421–429

(56) References Cited

U.S. PATENT DOCUMENTS

| 5,695,625 | A | * | 12/1997 | Yamada et al. | |
|---|---|---|---|---|---|
| 5,707,504 | A | * | 1/1998 | Jyouno et al. | |
| 5,762,771 | A | | 6/1998 | Yamada et al. | ............. 204/428 |
| 5,942,092 | A | * | 8/1999 | Weyl et al. | |
| 6,068,746 | A | * | 5/2000 | Kojima et al. | |

FOREIGN PATENT DOCUMENTS

JP          9-222416      8/1997      ......... G01N/27/409

* cited by examiner

Primary Examiner—Alex Noguerola
(74) Attorney, Agent, or Firm—Sughrue Mion, PLLC

(57) ABSTRACT

A gas sensor is provided which comprises a sensor element for detecting a component of a gas and a cup-shaped protector for covering a detecting section of the sensor element. The protector is dual-walled and have cup-shaped inner and outer protector members. The inner and outer protector members are constructed and arranged so that $g1>g2$ where $g1$ is the distance between an inner surface of a circumferential wall of the outer protector member and an outer surface of a circumferential wall of the inner protector member and $g2$ is the distance between an inner surface of a bottom wall of the outer protector member and an outer surface of a bottom wall of the inner protector member. The outer protector member has at the circumferential wall thereof a plurality of first gas holes. The inner protector member has at the circumferential wall thereof a plurality of second gas holes.

16 Claims, 10 Drawing Sheets

GAS SENSOR

BACKGROUND OF THE INVENTION

The present invention relates to a gas sensor such as an oxygen sensor, HC sensor and NOx sensor.

An example of a gas sensor includes a rod-shaped or tube-shaped sensor element having a detecting section for detecting a gas component at a tip end thereof, and a metal casing in which the sensor element is disposed. Such a gas sensor is attached to a predetermined attaching portion such as an exhaust pipe by means of a threaded portion formed on an outer periphery of a housing which forms part of the casing. The sensor element partially protrudes from the casing so as to allow the detecting section to be held in a gas to be measured. In many gas sensors, there is provided a protector for covering the detecting section and thereby protecting the detecting section from water and toxic substances. The protector has a peripheral wall formed with gas holes through which a gas to be measured such as exhaust gas is introduced into the protector for contact with the detecting section. In this connection, recently, in order to make higher the ability to protect the detecting section, a dual-walled protector having inner and outer protector members is widely used.

SUMMARY OF THE INVENTION

While the above described dual-walled protector can make higher the ability to protect the detecting section, the resistance to flow of the gas to be measured through the gas holes increases due to the dual-walled structure. In many cases, such an increase in flow resistance causes the speed with which the gas to be measured is exchanged between the inside and outside of the protector to become lower. For this reason, in case a concentration of a gas component to be measured changes rapidly, there is possibly caused a disadvantage, for example, that measurement of an air-fuel ratio lacks in accuracy.

The above described disadvantage will often become a serious problem when the gas sensor is a λ-type oxygen sensor. The λ-type oxygen sensor includes a detecting section constituted by an oxygen concentration cell element. The oxygen concentration cell element consists of a layer of oxygen ion conductive solid electrolyte such as zirconia and porous electrodes formed on the opposite sides of the solid electrolytic layer. The λ-type oxygen sensor detects an oxygen concentration on the basis of a variation of the electromotive force of the oxygen concentration cell element. The λ-type oxygen sensor can be responsive relatively sharply to a rise of the oxygen concentration, i.e., transition of the gas to be measured from a lean condition containing oxygen excessively to a rich condition containing combustible components excessively since the combustible components are adsorbed to the porous electrodes rapidly. However, in case of transition from the rich condition to the lean condition, a responsive delay in response to a fall of the oxygen concentration is liable to be caused since desorption of the combustible gas components from the porous electrodes can not be attained so rapidly as the adsorption thereof and in addition for the reason of the above described delay in exchange of the gas between the inside and outside of the protector.

Further, a responsive delay in response to a fall of the oxygen concentration will cause the following problem. An engine control unit performs such a combustion control that shifts the gas to be measured to a rich condition side (i.e., a combustion control that causes an intake mixture to shift to a rich side) when the output of the oxygen sensor falls to a certain constant level. However, since the output of the sensor is not lowered until the gas to be measured is put into a considerably lean condition, the combustion control for shifting the gas to be measured to a rich condition side is inevitably delayed. When the combustion control for shifting the gas to be measured to a rich condition side starts at long last, the output of the sensor is caused to rise relatively sharply. In response to this, the engine control unit stops the combustion control before the gas to be measured is put into a sufficiently rich condition (i.e., before an intake mixture becomes sufficiently rich). As a result, the gas to be measured is controlled under a condition of being shifted to a lean condition side at all times. Namely, a so-called lean shift control, i.e., a control for causing the gas to be measured to shift to a lean condition side tends to be performed. This can be regarded as a disadvantage caused by the fact that the behavior of the sensor at the time of a rise of its output is not equivalent to that at the time of a fall of its output.

It is accordingly an object of the present invention to provide a gas sensor which has an improved responsiveness, particularly at the time of a fall of its output.

It is a further object of the present invention to provide a gas sensor of the foregoing character which can decrease the difference between the responsiveness at the time when its output rises and the responsiveness at the time when its output falls.

It is a further object of the present invention to provide a gas sensor of the foregoing character which is particularly suited for use as an air-fuel ratio sensor for automotive vehicles and is therefore particularly useful from an anti-pollution preventing point of view.

To accomplish the above objects, there is provided according to an aspect of the present invention a gas sensor which comprises a sensor element having at a tip end portion thereof a detecting section for detecting a component of a gas to be measured, a casing accommodating therewithin the sensor element and having an open end portion from which the detecting section protrudes, and a protector attached to the open end portion of the casing for covering the detecting section. The protector is cup-shaped and has a bottom wall and a circumferential wall. The circumferential wall is dual-walled and includes an inner circumferential wall section and an outer circumferential wall section. The outer circumferential wall section of the protector has a first gas hole. The inner circumferential wall section of the protector has a second gas hole. The bottom wall of the protector has a bottom gas hole. When the direction of the tip end portion of the sensor element is referred to as forward, the first gas hole is disposed forward of the second gas hole and a front end of the sensor element is disposed forward of the second gas hole such that a gas to be measured is caused to flow rearward within a space between the inner and outer circumferential wall sections and forward within a space around the detecting section.

According to another aspect of the present invention, there is provided a gas sensor which comprises a sensor element having at a tip end portion thereof a detecting section for detecting a component of a gas to be measured, a casing accommodating therewithin the sensor element and having an open end portion from which the detecting section protrudes, and a cup-shaped protector attached to the open end portion of the housing for covering the detecting section. The protector is dual-walled and has cup-shaped inner and outer protector members which are bottomed. The inner and outer protector members have circumferential walls between which a predetermined space is defined. The space is determined so as to satisfy a relation of g1>g2 where g1 is the distance between an inner surface of the circumferential wall of the outer protector member and an outer surface of the circumferential wall of the inner protector member and g2 is the distance between an inner surface of a bottom wall of the outer protector member and an outer surface of a bottom wall of the inner protector member. The outer protector member has at the circumferential wall thereof a plurality of first gas holes. The inner protector member has at the circumferential wall thereof a plurality of second gas holes. When the direction of the tip end portion of the sensor element is referred to as forward, the first gas holes are disposed forward of the second gas holes. A front end of the sensor element is disposed forward of the second gas holes. The inner and outer protector members have at bottom walls thereof bottom gas holes.

BRIEF DESCRIPTION OF THE DRAWINGS

FIGS. 8 to 11A and 11B are views for illustration of a process of joining the protector and the housing of the gas sensor of FIG. 1.

DESCRIPTION OF THE PREFERRED EMBODIMENTS

Figure 1:
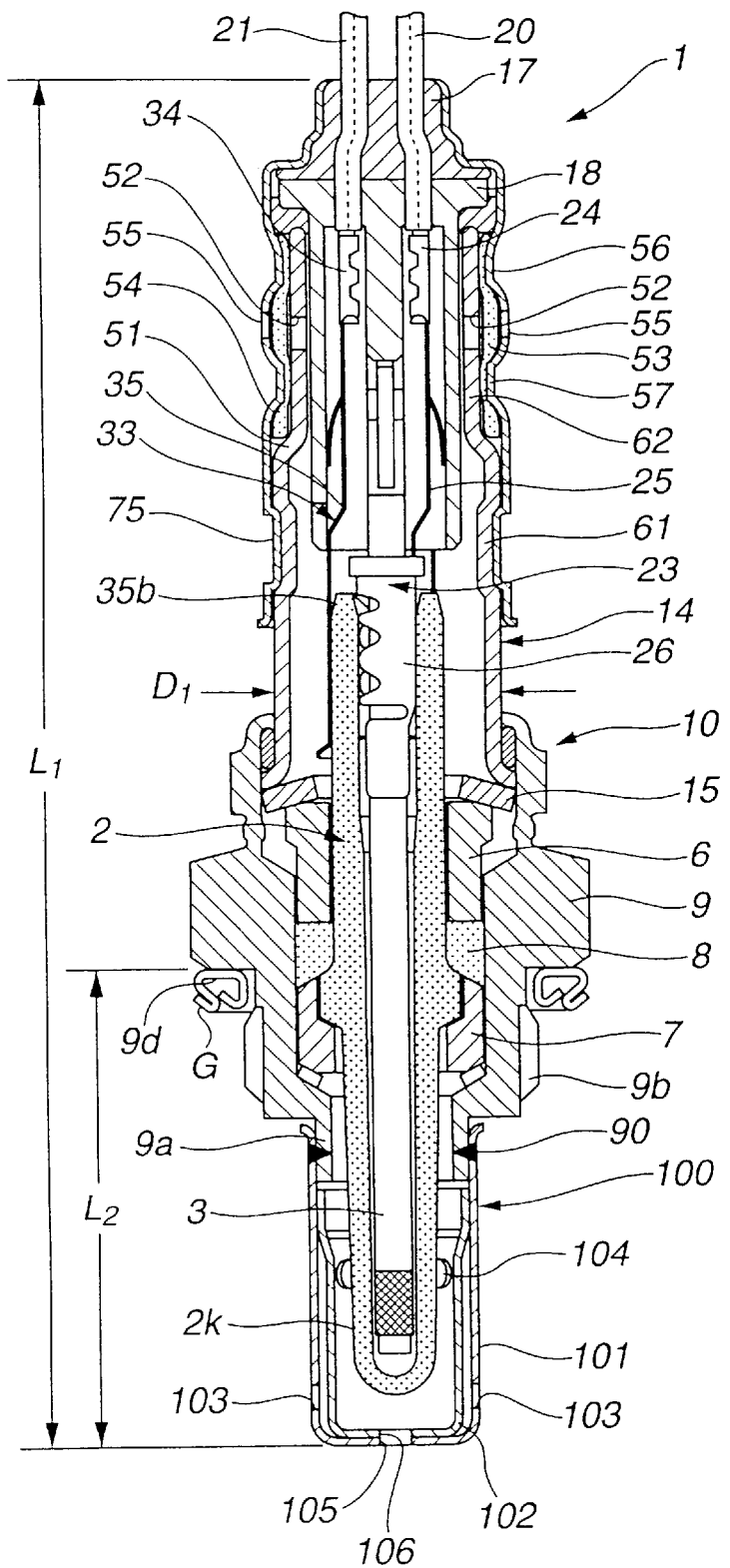
FIG. 1 is a sectional view of a gas sensor according to an embodiment of the present invention.

Referring first to FIG. 1, a gas sensor according to an embodiment of the present invention is shown as an oxygen sensor and generally indicated by 1. The oxygen sensor 1 is of the type generally called a λ sensor and includes an oxygen sensor element 2 in the form of a tube closed at one end thereof, and a heater 3 in the form of a rod and made of ceramic. The oxygen sensor element 2 is formed of an oxygen ion conductive solid electrolyte. Typical examples of such a solid electrolyte are $Y_2O_3$ and $ZrO_2$ containing a solid solution of CaO. However, solid solutions of $ZrO_2$ and an oxide of another alkaline earth metal or rare earth metal can be used in place thereof. Further, $ZrO_2$ serving as a base of the solid solution may contain $HfO_2$.

Figure 2:
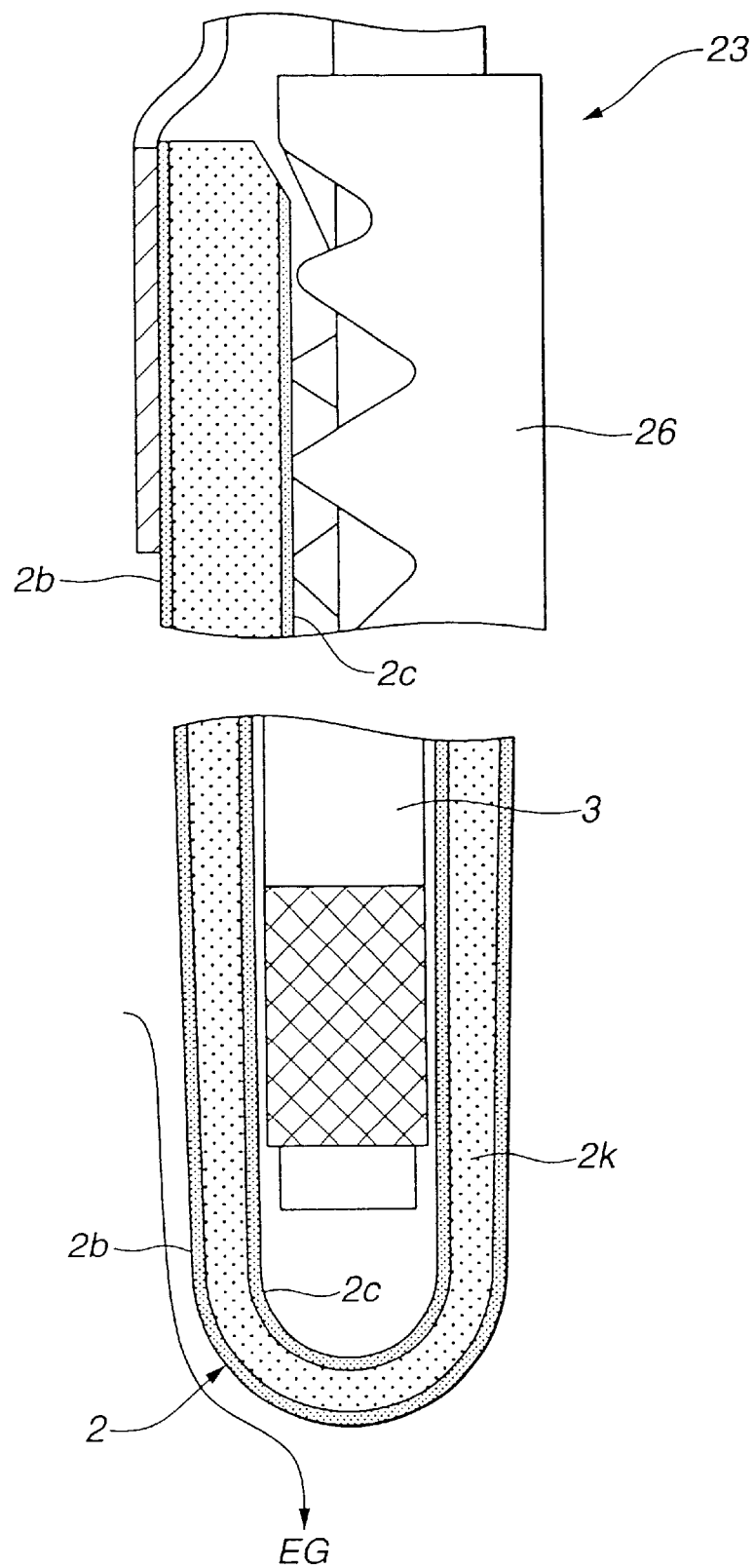
FIG. 2 is an enlarged view of a portion of the gas sensor of FIG. 1, i.e., a portion adjacent a place where a heater and an oxygen sensor element contact with each other.

A casing 10 is provided to enclose therein the sensor element 2. The sensor element 2 is supported fixedly upon the casing 10 by way of insulators 6 and 7 and ceramic powder 8 of talc which are disposed to surround an intermediate portion thereof. By this, the sensor element 2 is electrically insulated from the casing 10 while extending through the same. The casing 10 includes a tubular housing 9 having an externally threaded portion 9b for attaching the oxygen sensor 1 to a mount such as an exhaust pipe (not shown). The casing 10 further includes a tubular, inner casing member 14 connected to an end of the housing 9 in such a manner as to have an inner space in communication with an inner space of the housing 9. Further, as shown in FIG. 2, the sensor element 2 has at the inner and outer surfaces thereof a pair of electrode layers 2b and 2c which are disposed so as to cover all the inner and surfaces, respectively. Both of the electrode layers 2b and 2c are adapted to constitute porous electrodes such as Pt porous electrodes having a reversible catalytic function (oxygen dissociation catalytic function) toward an oxygen molecule dissociation reaction for injecting oxygen into the solid electrolyte constituting the oxygen sensor element 2 and an oxygen recombination reaction for releasing oxygen from the solid electrolyte. Of those electrode layers, the outer electrode layer 2b serves as a detection side porous electrode and the inner electrode layer 2c serves as a reference side porous electrode (hereinafter also referred to as a detection side porous electrode 2b and a reference side porous electrode 2c).

In the meantime, description of the oxygen sensor 1 will hereinlater be made by referring the direction of the closed, tip end of the oxygen sensor element 2 as forward or front side and the opposite direction as rearward or rear side.

Firstly, to the rear side open end portion of the housing 9 is attached by crimping the inner casing member 14 by interposing a ring 15 between an insulator 6 and the inner casing member 14. To the inner casing member 14 is fittingly fixed a tubular, outer casing member 54. The upper open end of the outer casing member 54, when observed in FIG. 1, is closed by a grommet 17 which is an elastic seal member and made of an elastic material such as rubber. On the inner side of the grommet 17 is provided a ceramic separator 18. Lead wires 20 and 21 for the oxygen sensor element 2 and lead wires for the heater 3 (though not shown since they are hidden by the lead wires 20 and 21) are disposed so as to extend through the ceramic separator 18 and the grommet 17.

One lead wire 20 for the oxygen sensor element 2 is electrically connected to the electrode layer 2c (refer to FIG. 2) at the inner side of the sensor element 2 by way of a terminal assembly 23 consisting of a connector 24, a leader line 25 and an inside electrode connector 26. On the other hand, the other lead wire 21 is electrically connected to the electrode layer 2b at the outer side of the sensor element 2 by way of another terminal assembly 33 consisting of a connector 34, a leader line 35 and an outside electrode connector 35b.

In this instance, when the temperature of the exhaust gas is sufficiently high, the sensor element 2 is heated by the exhaust gas and activated. However, when the temperature of the exhaust gas is low at the time of, for example, cold start of the engine, the sensor element 2 is forced to be heated by the heater 3 such as a ceramic heater and thereby activated. The heater 3 is held fixedly within the sensor element 2 by means of the terminal assembly 23.

Then, as shown in FIG. 1, the outer casing member 54 is nearly coaxially connected to the rear end portion of the inner casing member 14. The inner casing member 14 is formed with a stepped portion 51 and has on the axially front side of the stepped portion 51 a first section 61 and on the axially rear side of the stepped portion 51 a second section 62. The second section 62 is formed with a plurality of gas holes 52. Disposed around the second section 62 is a tubular filter 53 which closes the gas holes 52. The filter 53 is covered by the outer casing member 54 which is formed with a plurality of auxiliary gas holes 55 arranged in an array around the circumferential wall with equal intervals. Further, on the axially opposite sides of the array of the auxiliary gas holes 55 are formed a pair of annular, filter crimping portions 56 and 57 which cooperate with the second section 62 of the inner casing member 14 to compress and fixedly hold therebetween the filter 53. In the meantime, the filter 53 is formed from a water repellent filter (e.g., sold under the trade name of Gore-Tex by Japan Gore-Tex Inc.) which prevents passage of liquid containing water as a major constituent, such as a drop of water but allows passage of air and/or gas such as water vapor. The outer casing member 54 is further adapted to lie over the first section 61 of the inner casing member 14. The overlaid portion of the outer casing member 54 is formed into an annular crimped portion 75. By the crimped portion 75, the outer casing member 54 is connected to the inner casing member 14.

The housing 9 has an open front end portion which serves as a protector attaching portion 9a. The sensor element 2 has a front end potion, i.e., a detecting section 2k which protrudes from the housing 9. A cup-shaped protector 100 is attached to the protector attaching portion 9a so as to cover the detecting section 2k in a way as to provide a predetermined space around the detecting section 2k. The protector 100 is dual-walled and includes a cup-shaped, outer protector member 101 and a cup-shaped, inner protector member 102 disposed concentrically or coaxially within the outer protector member 101.

Figure 3:
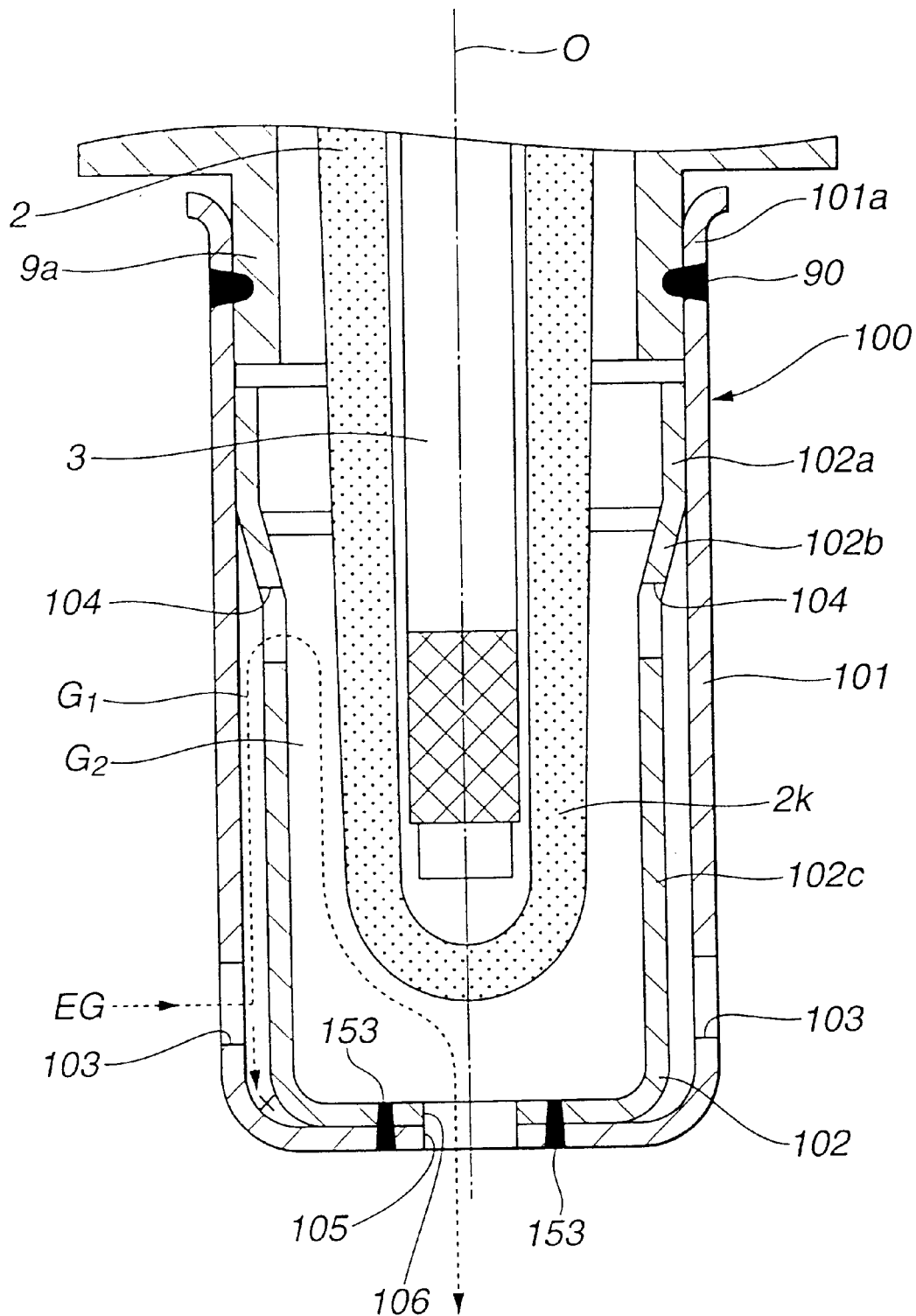
FIG. 3 is an enlarged view of a portion of the gas sensor of FIG. 1.

As shown in FIG. 3, the inner protector member 102 has a tapered, annular shoulder 102b at an axially intermediate, circumferential wall portion located adjacent the upper end thereof. The inner protector member 102 has a first circumferential wall portion 102a and a second circumferential wall portion 102c on the axially opposite sides of the shoulder 102b. The first circumferential wall portion 102a is constituted by a larger diameter open end portion and adapted to fit in the outer protector member 101. The second circumferential wall portion 102c is smaller in diameter than the first circumferential wall portion 102a. By this, a predetermined space G1 is provided between the inner surface of the circumferential wall of the outer protector member 101 and the outer surface of the circumferential wall of the inner protector member 102.

Figure 5:
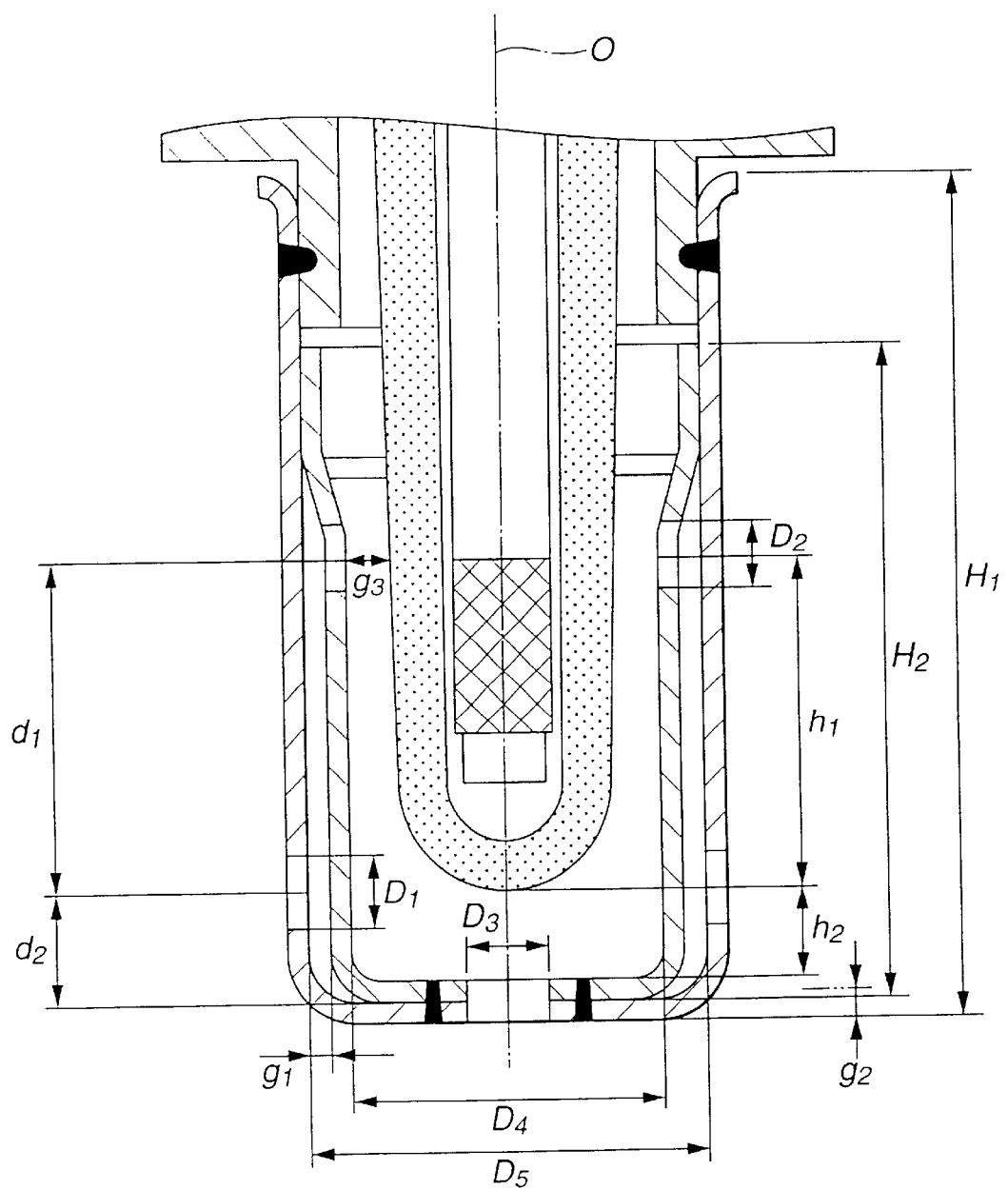
FIG. 5 is an enlarged, fragmentary sectional view for illustration of the size of the protector of the gas sensor of FIG. 1.

The outer protector member 101 and the inner protector member 102 have at bottom walls thereof circular, concentric, bottom gas holes 105 and 106 which are of the same diameter. The bottom walls are joined together at welded portions 153 which are formed by, for example, resistant welding such as spot welding. In this embodiment, the welded portions 153 are arranged so as to surround the bottom gas holes 105 and 106. In this connection, as shown in FIG. 5, assuming that g1 is the distance between the inner surface of the circumferential wall of the outer protector member 101 and the outer surface of the circumferential wall of the inner protector member 102 and g2 is the distance between the inner surface of the bottom wall of the outer protector member 101 and the outer surface of the bottom wall of the inner protector member 102, the space G1 is determined so as to satisfy the relation of g1>g2. In this embodiment, the relation is satisfied since g2 is zero. In the meantime, a little clearance may be provided between the inner surface of the bottom wall of the outer protector member 101 and the outer surface of the bottom wall of the inner protector member 102 so long as g1>g2 is satisfied.

The circumferential wall of the outer protector member 101 is formed with a plurality of (eight in this embodiment) first circular gas holes 103 which are arranged in an array therearound and at equal intervals. Further, the circumferential wall of the inner protector member 102 is formed with a plurality of (eight in this embodiment) second circular gas holes 104 which are arranged in an array therearound and at the same angular intervals as the first gas holes 103. The first gas holes 103 and the second gas holes 104 are disposed at axially different positions, i.e., at positions axially spaced from each other. Namely, when the direction of the tip end of the sensor element 2 is referred to as "forward", the first gas holes 103 are disposed forward of the second gas holes 104.

Figure 4A:
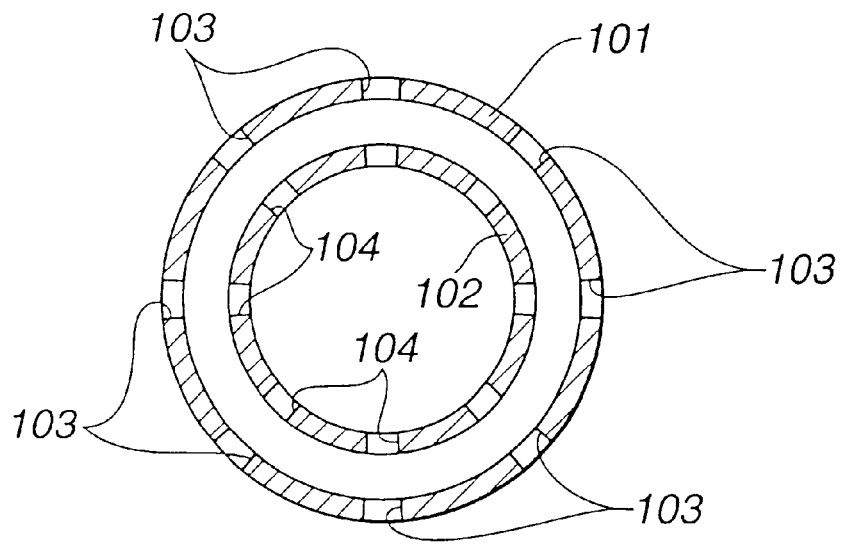
FIG. 4A is a cross sectional view of a protector of the gas sensor of FIG. 1.
Figure 4B:
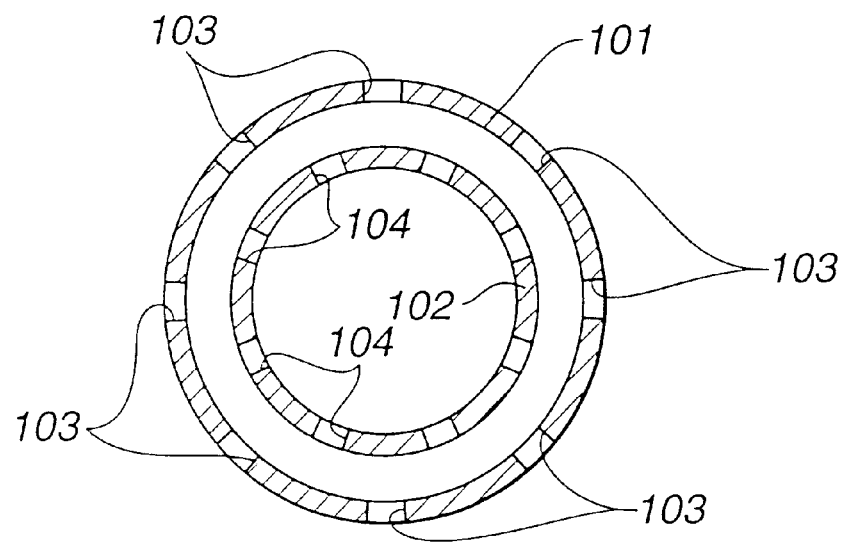
FIG. 4B is a view similar to FIG. 4A but shows a variant of the protector of FIG. 4A.
Figure 7:
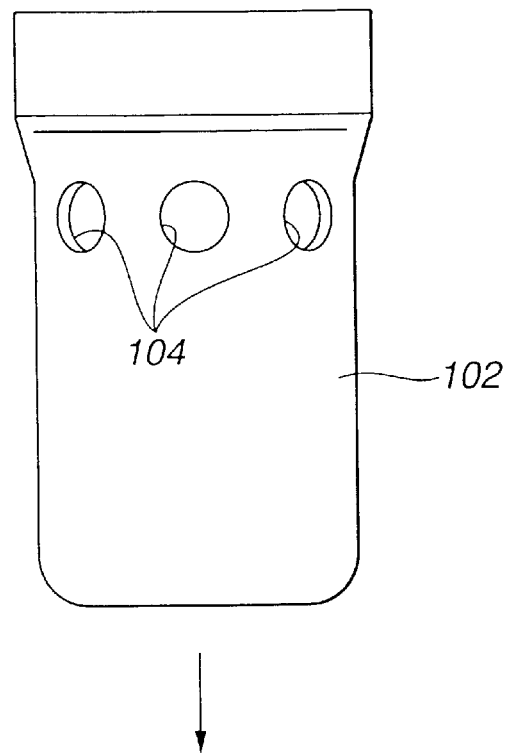
FIG. 7 is a view for illustration of a process of assembling a protector.
Figure 7:
Figure 7:
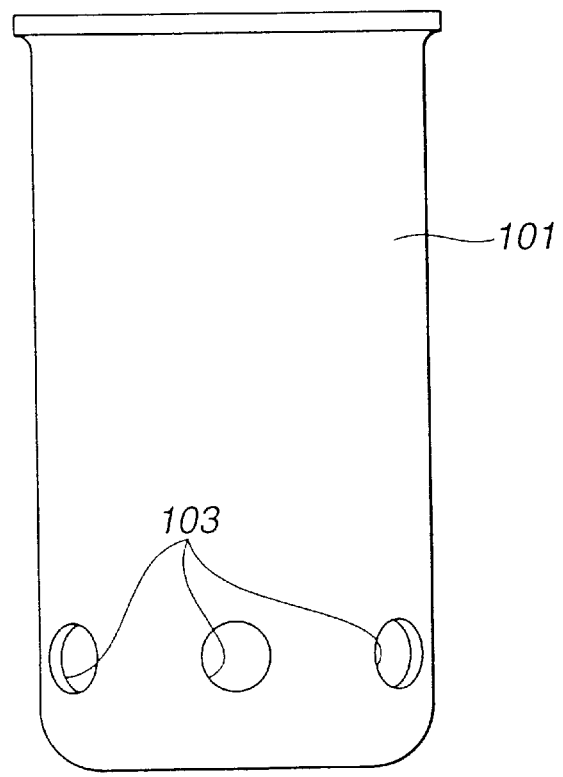

As shown in FIG. 7, the outer protector member 101 does not have any gas holes at the circumferential wall thereof except for the array of the first gas holes 103. On the other hand, the inner protector member 102 does not have any gas holes at the circumferential wall thereof except for the array of the second gas holes 104. As shown in FIG. 4A, the first gas holes 103 and the second gas holes 104 are arranged at the same angular positions with respect to the circumferential direction of the outer protector member 101 and the inner protector member 102. However, as shown in FIG. 4B, the first gas holes 103 and the second gas holes 104 may be arranged at the angular positions different from each other.

Further, as shown in FIG. 5 (also reference being made to FIG. 3), assuming that d1 denotes, with respect to the axial direction of the sensor element 2, i.e., along the axis O thereof, the distance between first gas holes 103 and the second gas holes 104 and d2 denotes the distance between the inner surface of the bottom wall of the outer protector member 101 and the first gas holes 103, the first and second gas holes 103 and 104 are arranged so as to satisfy the relation of d1>d2. In this connection, the distance between the gas holes 102 and 103 is herein intended to indicated the distance between the center axes of the gas holes. In case the gas holes are not circular, the said distance indicates the geometrical centers of gravity of the gas holes. Similarly, assuming that h1 is the distance between the second gas holes 104 and the front end of the sensor element 2 and h2 is the distance between the front end of the sensor element 2 and the inner surface of the bottom wall of the inner protector member 102, the second gas holes 104 and the front end of the sensor element 2 are arranged so as to satisfy the relation of h1>h2.

As shown in FIG. 3, the protector 100 is attached to the protecting attaching portion 9a of the housing 9 by inserting the protector attaching portion 9a into an upper open end portion 101a of the protector 100 and forming welded portions 90 at the joining sections of the protector attaching portion 9a and the upper end portion 101a by laser welding or spot welding for thereby joining them together.

Hereinafter, the operation of the oxygen sensor 1 will be descried.

In the oxygen sensor 1 shown in FIG. 1, the air serving as a reference gas is introduced through the filter 53 of the outer casing member 54, while on the other hand, the outer surface of the sensor element 2 is brought into contact with a gas to be measured which is, for example, an exhaust gas EG emitted from an internal combustion engine and introduced through the gas holes 103 and 104 of the protector 100. By this, there is produced in the sensor element 2 an oxygen concentration cell electromotive force corresponding to the difference in the oxygen concentration between the inside and outside of the sensor element 2. By taking out the oxygen concentration cell electromotive force from the electrode layers 2b and 2c by way of the lead wires 21 and 20 for use as a signal representative of the oxygen concentration in the exhaust gas, the oxygen concentration in the exhaust gas can be detected. This kind of oxygen sensor 1 exhibits such characteristics that a concentration cell electromotive force produced thereby varies sharply when the exhaust gas composition indicates that the air-fuel mixture is close to an ideal air-fuel ratio, and therefore widely used for detection of the air-fuel ratio.

Since the protector 100 for protecting the detecting section 2k is dual-walled, the detecting section 2k is protected from being covered with water and poisoning. Further, by constructing so that the gas holes 103 and 104 of the inner and outer protector members 101 and 102 have such a positional relation as described above, the detection can be accurate even if the concentration of a gas component to be measure changes rapidly. Specifically, in case the composition of the exhaust gas EG changes rapidly in response to a change of the air-fuel ratio from the lean side to the rich side, the output of the sensor can follow such a change with a little lag, thus making it possible to detect the air-fuel ratio accurately. In this connection, the reason why will become apparent as the description proceeds further.

Since as shown in FIG. 3, the outer protector member 101 and the inner protector member 102 are disposed so as to be joined together at the bottom walls thereof, there is not caused any flow of the exhaust gas EG from the first gas holes 103 to the bottom gas holes 105, i.e., any flow through a short way but almost all of the exhaust gas EG introduced into the space G1 is caused to flow from the first gas holes 103 toward the second gas holes 104. Then, within the inner protector member 102, due to the provision of the bottom gas holes 105 and 106, there tends to be produced such a gas flow which is directed from the second gas holes 104 toward the bottom gas holes 105 and 106 through the space G2 between the sensor element 2 and the inner protector member 102. By this, the exhaust gas EG is caused to flow along the peripheral surface of the detecting section 2k at a relatively large speed and thereafter discharged from the bottom gas holes 105 and 106 promptly. This is considered effective for promoting exchange of the gas between the rich condition and the lean condition and therefore effective for promoting desorption of the combustible gas component at the time of a fall of the output of the oxygen sensor 1.

In this instance, as shown in FIG. 2, the detecting section 2k constitutes an oxygen concentration cell element consisting of the detection side porous electrode 2b formed on one side (outer side) of an oxygen-ion conductive solid electrolytic layer and the oxygen reference side porous electrode 2c formed on the other side (inner side) of the solid electrolytic layer. The exhaust gas EG directed from the second gas holes 104 to the bottom gas holes 105 and 106 is brought into contact with the surface of the detection side porous electrode 2b while moving at a relatively high speed. For example, in case of measurement of the air-fuel ratio by using a λ sensor, a prior art λ sensor tends to cause a responsive delay when the composition of the exhaust gas changes in response to a change of the air-fuel ratio from the rich side to the lean side since the speed of desorption of the combustible gas component is lower than the speed of adsorption. However, by the above described structure, there is caused a delay in bringing the exhaust gas EG into contact with the detection side porous electrode 2b, and the exhaust gas EG can contact at a large area with the detection side porous electrode 2b, thus decreasing the difference between the responsiveness at the time the sensor output falls and the responsiveness at the time the sensor output rises and therefore making it possible to make considerably higher the accuracy in detection.

More specifically, according to the present invention, the gas sensor 1 is constructed so that the distance g1 is larger than the distance g2 and the first gas holes 103 are disposed forward of the second gas holes 104. By this, the gas to be measured takes a long way or roundabout way before flowing into the inner protector member 102. Accordingly, there is caused a delay in flowing of the gas to be measured into the inner protector member 102 and therefore a delay in changing of the gas within the inner protector member 102 from the rich condition to the lean condition. By this delay, the gas within the inner protector member 102 is held in a lean condition for a longer time as compared with the time in case of a gas sensor which is not adapted to take the above described roundabout way. By this, for example, desorption of the combustible component can be performed sufficiently. As a result, in case a feedback control of the combustion of the engine is first performed in response to a change of the gas to be measured from a rich condition to a lean condition and thereafter the gas to be measured changes into a rich condition again, the output of the oxygen sensor is caused to rise again after falling sufficiently, thus making it possible to attain an accurate combustion control of the engine. Further, the above structure of this invention is effective for making the gas to be measure tend to flow along the detection side porous electrode 2b, thus making it possible to promote adsorption of the combustible gas component from the porous electrode 2b and therefore improve the accuracy in detection considerably.

In the meantime, various dimensions or sizes of the protector 100 shown in FIG. 5 can be set as follow. In the meantime, the numeral in the parenthesis indicates the particular size for the structure shown in FIG. 1.

D1 (opening area of first gas hole 103): 1 to 10 mm$^2$ (4.9 mm$^2$)

When D1 becomes smaller than 1 mm$^2$, the resistance to flow of the gas to be measured into the outer protector member 101 becomes too large, thus causing a bad influence on the accuracy in detection by the sensor 1. Further, when D1 exceeds 10 mm$^2$, it becomes difficult to cause a delay in inflow of the gas to be measured. Thus, before a fall of the output of the oxygen sensor 1 is completed, a rise of the output for making the air-fuel ratio richer starts, thus causing a possibility of deteriorating the accuracy in detection.

D2 (opening area of second gas hole 104): 1 to 10 mm$^2$ (4.9 mm$^2$)

When D2 becomes smaller than 1 mm$^2$, the resistance to flow of the gas to be measured into the outer protector member 101 becomes too large, thus causing a bad influence on the accuracy in detection by the sensor 1. Further, when D2 exceeds 10 mm$^2$, it becomes difficult to cause a delay in inflow of the gas to be measured. Thus, before a fall of the output of the oxygen sensor 1 is completed, a rise of the output for making the air-fuel ratio richer starts, thus causing a possibility of deteriorating the accuracy in detection. Further, when the opening area of D2 becomes too large (particularly, D2>D3, D3 will be described hereinlater), it may possibly become difficult for the gas to be released smoothly through the bottom gas holes 105 and 106.

D3 (opening area of bottom gas holes 105 and 106): 1 to 10 mm$^2$ (7 mm$^2$)

When D3 is smaller than 1 mm$^2$, the resistance to outflow of the gas to be measured becomes too large. Particularly, when D2>D3, there may possibly be caused a bad influence on the accuracy in detection. Further, when D3 exceeds 10 mm², a back flow of the gas to be measured tends to be caused, thus similarly causing a possibility of deteriorating the responsiveness. Further, depending on the sizes of D1 and D2, the outflow speed of the gas to be measured becomes too large, thus causing a possibility that the sensor cannot respond to a concentration variation of a gas component to be measured.

d1: 5 to 15 mm (7 mm)
d2: 1.5 to 5 mm (2.6 mm)
d1/d2: 1 to 10 (2.7)

When d1/d2 becomes smaller than 1, a larger part of the space G1 is formed on the axially forward side of the first gas holes 103. Thus, by the influence of the flow of gas into that part of the space G1, the flow of gas toward the second gas holes 104 is obstructed. This may possibly obstruct the exchange of gas within the protector 100. On the other hand, when d1/d2 exceeds 10, the passage extending from the first gas hole 103 to the second gas hole 104 becomes too long, thus causing the exchange of gas within the protector 100 to be obstructed.

g1: 0.3 to 1.5 mm (0.53 mm)

When g1 becomes smaller than 0.33 mm, the resistance to gas flow becomes too large, thus causing a possibility of the accuracy in detection being lowered. On the other hand, when g1 exceeds 1.5 mm, there may be caused a possibility that the speed of gas flow into the second gas holes 104 is lowered.

g3 (distance between inner circumferential surface of inner protector member 102 and outer surface of sensor element 2 when measured along center axis of second gas hole 104): 0.5 to 2.0 mm (1.0 mm)

When g3 becomes smaller than 0.5 mm, the resistance to gas flow becomes too large, thus causing a possibility that the accuracy in detection is lowered. On the other hand, when g3 exceeds 2.0 mm, there is caused a possibility that the speed of gas released from the bottom gas holes 105 and 106 is lowered.

h1: 5 to 20 mm (9 mm)
h2: 0.5 to 3.0 mm (1.0 mm)

When h1 becomes smaller than 5 mm, the length with which the sensor element 2 is brought into contact with the gas flow, becomes too short. Thus, when the concentration of the gas component to be measured varies, there is caused a possibility that the sensor 1 cannot respond to such a change. Further, when h1 exceeds 20 mm, the gas flow passage becomes too long, thus causing a possibility that exchange of gas within the protector 100 is obstructed. When h2 becomes smaller than 0.5 mm, the front end of the sensor element 2 goes closer to the bottom gas holes 105 and 106, thus causing a possibility that discharge of the gas is obstructed to deteriorate the accuracy in detection. Adversely, when h2 exceeds 3.0 mm, the protector 100 becomes needlessly long, thus causing a disadvantage from the point of view of making the sensor 1 compact.

H1 (length of outer protector member 101): 20.0 mm for instance

H2 (length of inner protector member 102): 15.4 mm for instance

Figure 6:
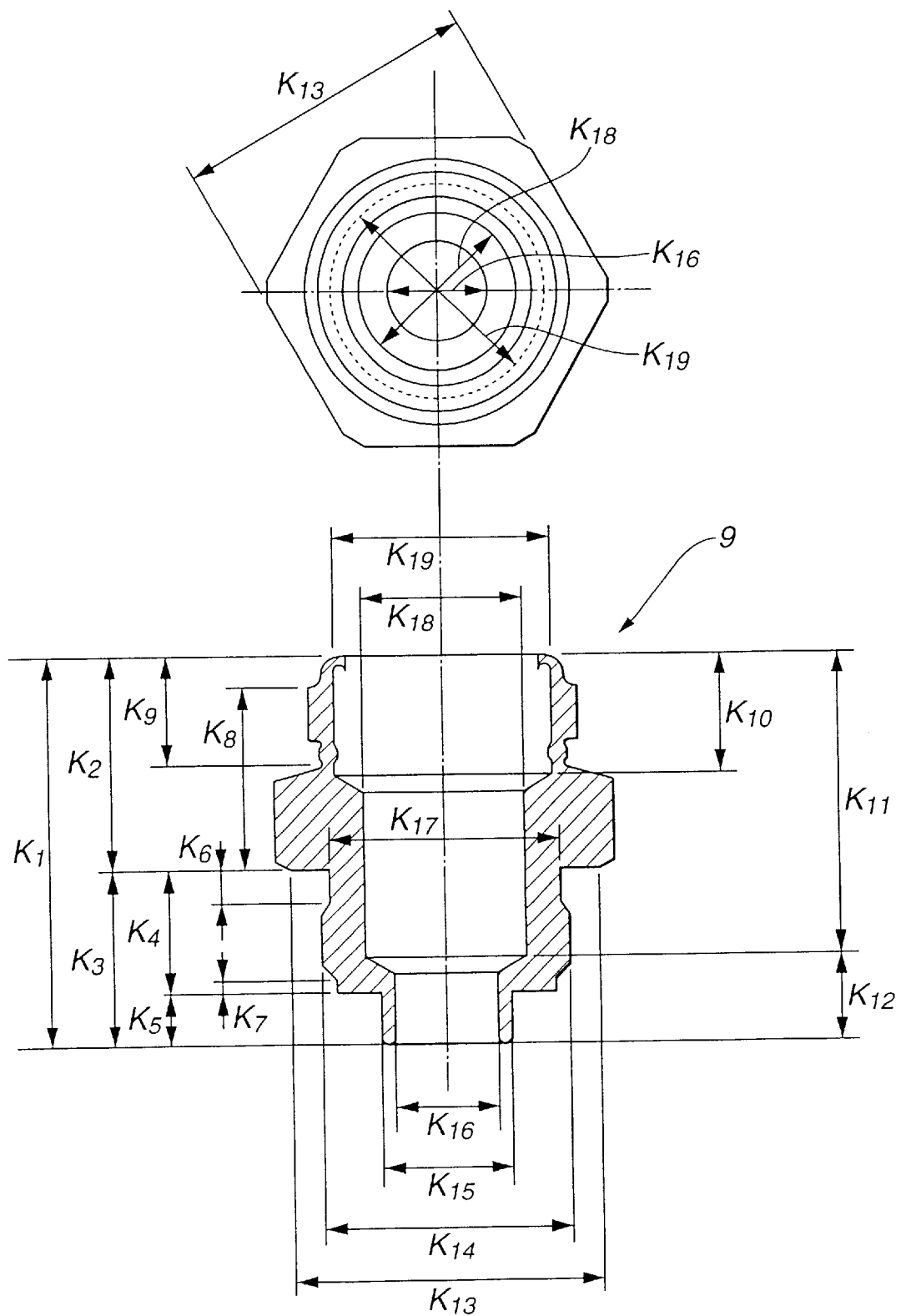
FIG. 6 is a view for illustration of the size of a housing of the gas sensor of FIG. 1.

Further, the sizes of various portions of the housing 9 shown in FIG. 6 can be set as follows, wherein the numerals in the parentheses are particular sizes for the structure shown in FIG. 1.

K1: 25 to 30 mm (29.6 mm)
K2: 13 to 17 mm (16.8 mm)
K3: 12.5 to 13.0 mm (12.8 mm)
K4: 8.8 to 9.2 mm (9 mm)
K5: 3.6 to 4 mm (3.8 mm)
K6: 1 to 2.5 mm (2 mm)
K7: 0.5 to 1.5 mm (1 mm)
K8: 12 to 14 mm (13.9 mm)
K9: 7 to 10 mm (9.6 mm)
K10: 7.5 to 10.5 mm (10 mm)
K11: 20.0 to 23.6 mm (23.1 mm)
K12: 5 to 7 mm (6.5 mm)
K13: 21.8 to 22.2 mm (22 mm)
K14: around M18, for instance
K15: 9.3 to 11.2 mm (9.5 mm)
K16: 7.3 to 7.7 mm (7.5 mm)
K17: 16.3 to 16.7 mm (16.5 mm)
K18: 11.4 to 11.8 mm (11.6 mm)
K19: 15.8 to 16.2 mm (16 mm)

Further, as shown in FIG. 1, the overall length L1 of the sensor 1 is about 84 mm. The length L2 from a gasket G support surface 9d of the housing 9 to the front end face of the protector 100 is about 29 mm.

Figure 8:
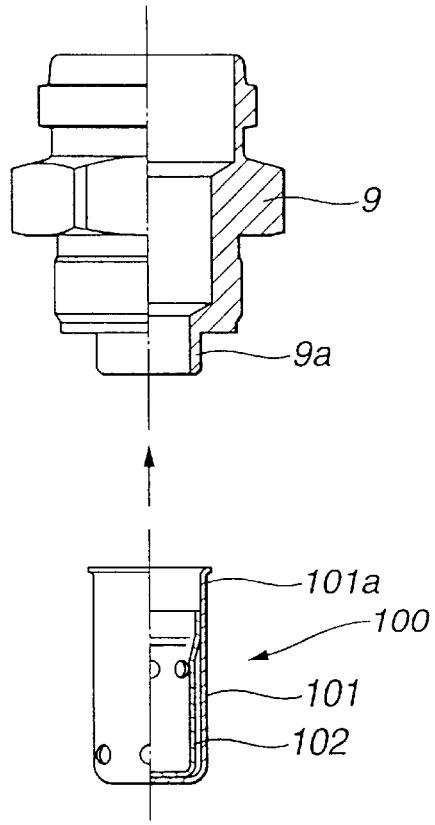
Figure 9:
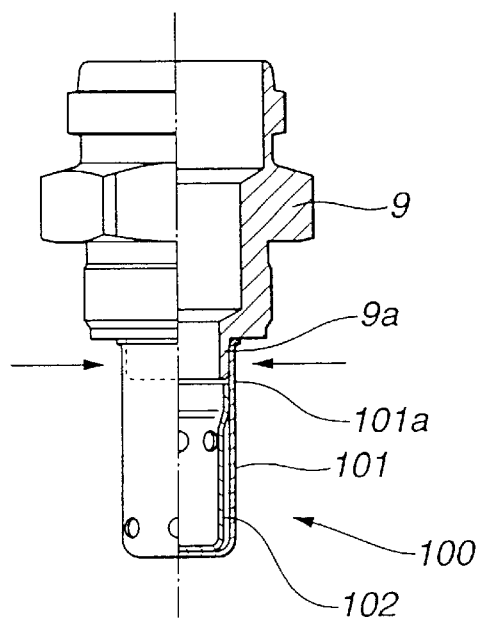
Figure 10:
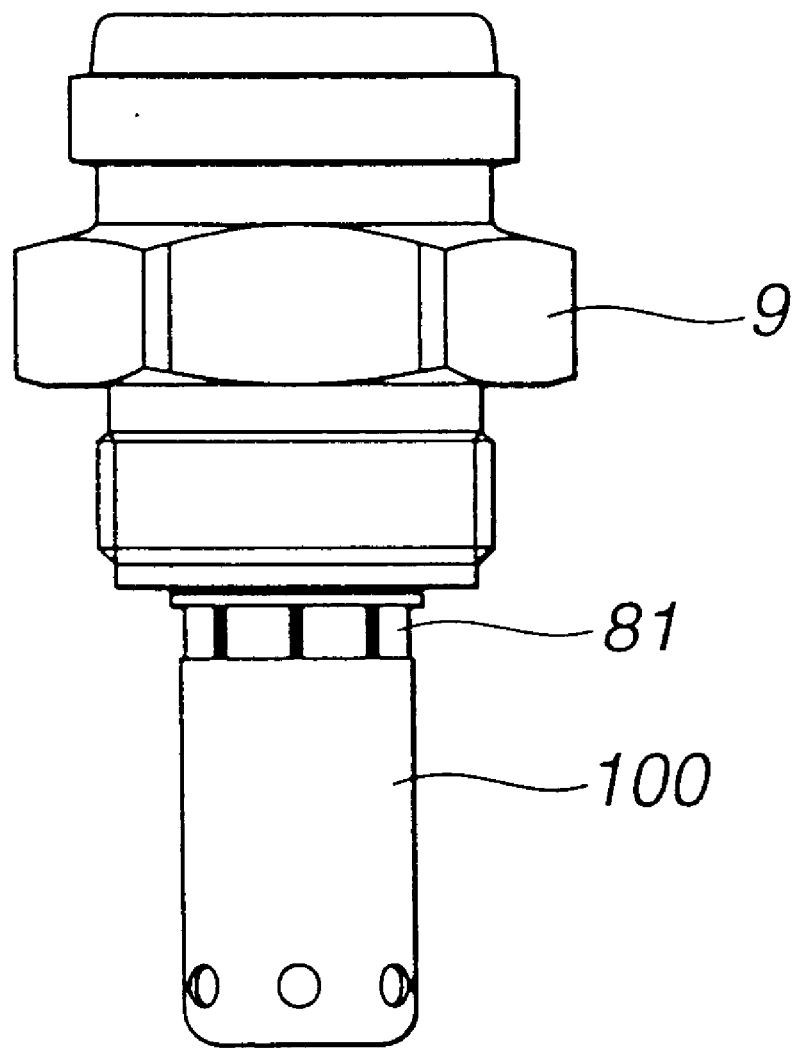

The protector 100 can be joined to the housing 9 by a crimped and welded portion 150 which is formed by the method shown in FIGS. 8 to 11. As shown in FIG. 8, the protector attaching portion 9a of the housing 9 is inserted into the attached portion 101a of the protector 100 until the open edge of the attached portion 101a abuts upon the end face of the housing 9. As shown in FIG. 9, under this condition, an axially intermediate section of the attached portion 101a is crimped radially toward the protector attaching portion 9a for thereby forming a crimped potion 81 as shown in FIG. 10. In this instance, an annular recess corresponding to the crimped portion 81 is formed in the protector attaching portion 9a.

Figure 11A:
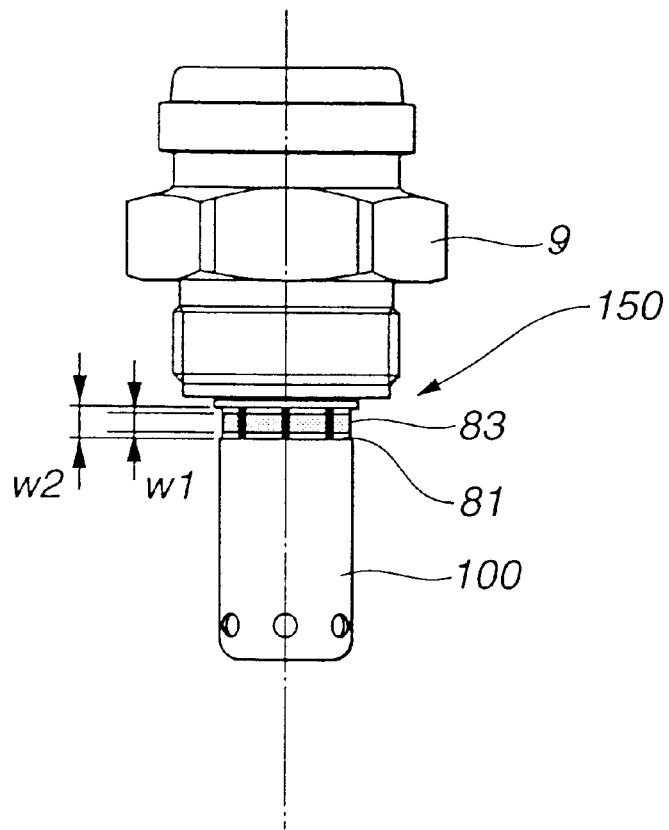
Figure 11B:
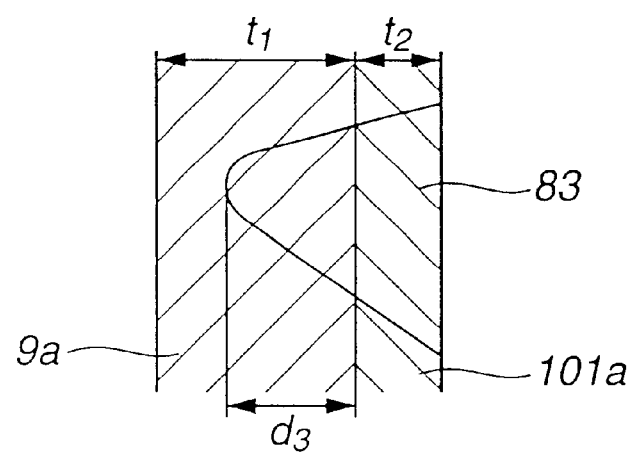

Then, as shown in FIG. 11A, the crimped portion 81 is formed with a circumferential welded portion 83 by, for example, laser welding, whereby to form a crimped-and-welded portion 150. In this instance, assuming that W1 denotes the width of the welded portion 83 and W2 denotes the width of the crimped portion 81, it is desired from the point of view of the joining strength that W1/W2 is equal to or larger than 0.5 (in the embodiment of FIG. 1, W1 is about 0.7 mm and We is about 1 mm so that W1/We is about 0.7). Further, as shown in FIG. 11B, in order that the protector attaching portion 9a can produce a sufficient force at crimping for obtaining a good crimped condition, the thickness t2 of the attached portion 101a (outer member) is desired to be set at 1 mm or less (in the embodiment of FIG. 1. t2 is about 0.4 mm). Further, the depth d3 by which the welded portion 83 goes into the protector attaching portion 9a (inner member) is desirable to be 0.3 mm from the joining strength point of view. However, if the welded portion 83 is formed so as to penetrate the protector attaching portion 9a (inner member) in the thickness direction thereof, there may possibly occur such a case that the joining strength is lowered due to the influence of welding defect, etc. Thus, it is desirable that the depth d3 is smaller than the thickness t1 of the protector attaching portion 9a.

By first forming the crimped portion 81 at the joint between the protector 100 and the protector attaching portion 9a for thereby making them fit more assuredly and then forming the welded portion 83 throughout the entire circumference thereof, the hermetic ability at the joint between them can be improved. For example, when the oxygen sensor 1 is cooled to a low temperature, there may possibly occur such a case that water vapor is condensed to deposit upon the outer surface of the protector 100. In this instance, if the welded portion 83 joining the housing 9 and the protector 100 together is defective, condensed vapor water may possibly intrude through a defective portion to wet the detection portion 2k or may cause a rust or the like dirt to adhere onto the same. However, since the housing 9 and the protector 100 are joined together by the crimped-and-welded portion 150. Such ingress of water drop and dirt can be prevented effectively and assuredly.

In the meantime, such welding throughout the circumference according to the prior art is carried out by first joining the protector and the attaching portion of the housing by loose fit or force fit and then forming the welded portion. However, by this method, there occurs such a case that good welding cannot be attained unless the difference between the inner diameter of the protector and the outer diameter of the attaching portion of the housing is strictly controlled. By the above structure, even if such a difference in diameter varies a little, they can fit together when the crimped portion 81 is formed, thus making it possible to dispense with the above described strict control of the size. As a result, the sensor can be produced with an improved efficiency and with an improved yielding rate.

In the meantime, the protector 100 and the protector attaching portion 9a of the housing 9 may be joined together by first forming an annular reduced diameter portion at the open end of the protector 100 by pressing or the like, then force-fitting the protector attaching portion 9a of the housing 9 in the reduced diameter portion and forming the welded portion at the reduced diameter portion. By force-fitting the protector attaching portion 9a in the reduced diameter portion, it becomes possible to prevent the open end portion of the protector 100 from tapering toward the opposite end, thus making it possible to reduce the rate at which a defective welded portion is caused.

Although the invention has been described as above by reference to certain embodiments of the invention, the invention is not limited to the embodiments described above. Modifications and variations of the embodiments described above will occur to those skilled in the art, in light of the above teachings. The scope of the invention is defined with reference to the following claims.

What is claimed is:

1. A gas sensor comprising:
    a sensor element having at a tip end portion thereof a detecting section for detecting a component of a gas to be measured;
    a casing accommodating therewithin the sensor element and having an open end portion from which the detecting section protrudes; and
    a cup-shaped protector attached to the open end portion of the casing for covering the detecting section;
    the protector being dual-walled and having cup-shaped inner and outer protector members;
    the outer protector member having at the circumferential wall thereof a plurality of first gas holes;
    the inner protector member having at the circumferential wall thereof a plurality of second gas holes;
    when the direction of the tip end portion of the sensor element is referred to as forward, the first gas holes being disposed forward of the second gas holes;
    a front end of the sensor element being disposed forward of the second gas holes;
    the inner and outer protector members having circumferential walls between which a predetermined space is defined, the space being determined so as to satisfy a relation of g1>g2 where g1 is the distance between an inner surface of the circumferential wall of the outer protector member and an outer surface of the circumferential wall of the inner protector member and g2 is the distance between an inner surface of a bottom wall of the outer protector member and an outer surface of a bottom wall of the inner protector member so that an exhaust gas is caused to flow rearward from the first gas holes through a space of the distance g1 to the second gas holes and forward within a space around the detecting section;
    the inner and outer protector members having at bottom walls thereof bottom gas holes for allowing an exhaust gas introduced through the second gas holes into the inner protector member to be discharged from the inner protector member through said bottom gas holes;
    the circumferential wall of the inner protector member having an annular shoulder and contacting the inner surface of the circumferential wall of the outer protector member at a rearward end of said shoulder, the rearward end of said shoulder being disposed rearward of the second gas holes; and
    the outer protector member having no gas holes at the circumferential wall thereof except for said first gas holes disposed forward of the second gas holes.

2. A gas sensor according to claim 1, wherein the detecting section of the sensor element comprises an oxygen concentration cell element having a detection side porous electrode on one of opposite sides of an oxygen-ion conductive solid electrolytic layer and an oxygen reference side porous electrode on the other of the opposite sides, such that the gas to be measured directed from the second gas holes to the bottom gas holes flows along the surface of the detection side porous electrode.

3. A gas sensor according to claim 1, wherein the bottom gas hole of the outer protector member and the bottom gas hole of the inner protector member are formed concentrically.

4. A gas sensor according to claim 1, wherein the inner surface of the bottom wall of the outer protector member and the outer surface of the bottom wall of the inner protector member are in contact with each other.

5. A gas sensor according to claim 1, wherein the first gas holes are arranged in an array around the circumferential wall of the outer protector member with equal intervals, and the second gas holes are arranged in an array around the circumferential wall of the inner protector member with equal intervals.

6. A gas sensor according to claim 1, wherein the first gas holes and the second gas holes are arranged so as to satisfy a relation of d1>d2 wherein with respect to the axial direction of the sensor element, d1 is the distance between the first gas holes and the second gas holes and d2 is the distance between the inner surface of the bottom wall of the outer protector member and the first gas holes.

7. A gas sensor according to claim 1, wherein the second gas holes and the front end of the sensor element are arranged so as to satisfy a relation of h1>h2 where with respect to the axial direction of the sensor element, h1 is the distance between the second gas holes and the front end of the sensor element and h2 is the distance between the front end of the sensor element and the inner surface of the bottom wall of the inner protector member.

8. A gas sensor according to claim 1, wherein all of the first gas holes are disposed forward of the second gas holes.

9. A gas sensor according to claim 1, wherein the inner protector member does not have gas holes at the circumferential wall thereof except for said second gas holes disposed rearward of said first gas holes.

10. A gas sensor according to claim 1, wherein the outer protector member does not have any gas holes at the circumferential wall thereof except for said first gas holes, the inner protector member does not have any gas holes at the circumferential wall thereof except for said second gas holes, and each of said first gas holes being disposed forward of each of said second gas holes.

11. A gas sensor according to claim 1, wherein $D2 \leq D3$ where $D2$ is an opening area of each of the second gas holes and $D3$ is an opening area of each of the bottom gas holes.

12. A gas sensor according to claim 1, wherein the distance $g1$ is within the range from 0.3 to 1.5 mm.

13. A gas sensor according to claim 1, wherein the casing has a tubular housing to which the protector is joined by one of laser welding and spot welding.

14. A new gas sensor comprising:
- a sensor element having at a tip end portion thereof a detecting section for detecting a component of a gas to be measured;
- a casing accommodating therewithin the sensor element and having an open end portion from which the detecting section protrudes; and
- a cup-shaped protector attached to the open end portion of the casing for covering the detecting section;
- the protector being dual-walled and having cup-shaped inner and outer protector members;
- the outer protector member having at the circumferential wall thereof a plurality of first gas holes;
- the inner protector member having at the circumferential wall thereof a plurality of second gas holes;
- when the direction of the tip end portion of the sensor element is referred to as forward, the first gas holes being disposed forward of the second gas holes;
- a front end of the sensor element being disposed forward of the second gas holes;
- the inner and outer protector members having circumferential walls between which a predetermined space is defined, the space being determined so as to satisfy a relation of $g1>g2$ where $g1$ is the distance between an inner surface of the circumferential wall of the outer protector member and an outer surface of the circumferential wall of the inner protector member and $g2$ is the distance between an inner surface of a bottom wall of the outer protector member and an outer surface of a bottom wall of the inner protector member so that an exhaust gas is caused to flow rearward from the first gas holes through a space of the distance $g1$ to the second gas holes and forward within the space around the detecting section;
- the inner and outer protector members having at bottom walls thereof bottom gas holes for allowing an exhaust gas introduced through the second gas holes into the inner protector member to be discharged from the inner protector member through said bottom gas holes; and
- the circumferential wall of the inner protector member having a first circumferential wall portion with an outer surface contacting the inner surface of the circumferential wall of the outer protector member, a second circumferential wall portion disposed forward of the first circumferential wall portion and having a smaller diameter than the first circumferential wall portion so as to cooperate with the circumferential wall of the outer protector member to define therebetween the space of the distance $g1$, and a tapered, annular shoulder between the first circumferential wall portion and the second circumferential wall portion, a forward end of the outer surface of said first circumferential wall portion being disposed rearward of the second gas holes; and
- the outer protector member having no gas holes at the circumferential wall thereof except for said first gas holes disposed forward of the second gas holes.

15. A gas sensor according to claim 14, wherein the distance $g1$ is within the range from 0.3 to 1.5 mm.

16. A gas sensor according to claim 14, wherein the casing has a tubular housing to which the protector is joined by one of laser welding and spot welding.

* * * * *